United States Patent [19]

Bissonnette et al.

[11] Patent Number: 5,409,005
[45] Date of Patent: Apr. 25, 1995

[54] TRANSCRANIAL DOPPLER PROBE WHEEL AND TRACK/BAR FIXATION ASSEMBLY

[75] Inventors: Bruno Bissonnette, North York, Canada; Stephan P. Nebbia, Amherst, N.Y.; Andras Boross, Belmont, Calif.

[73] Assignee: MedaSonics, Inc., Fremont, Calif.

[21] Appl. No.: 133,750

[22] Filed: Oct. 7, 1993

[51] Int. Cl.$^6$ .............................................. A61B 8/00
[52] U.S. Cl. ............................ 128/660.01; 128/662.04
[58] Field of Search .................. 128/661.07–661.10, 128/662.03–662.04

[56] References Cited

U.S. PATENT DOCUMENTS

| | | | |
|---|---|---|---|
| 4,442,844 | 4/1984 | Navach | 128/662.04 |
| 4,483,344 | 11/1984 | Atkov et al. | 128/661 |
| 4,817,621 | 4/1989 | Aaslid | 128/662.03 |
| 4,920,966 | 5/1990 | Hon et al. | 128/662.03 |
| 4,947,853 | 8/1990 | Hon | 128/662.03 |
| 5,022,401 | 6/1991 | Eden | 128/662.03 |
| 5,070,880 | 12/1991 | Gomez et al. | 128/661.08 |
| 5,167,165 | 12/1992 | Brucher et al. | 128/662.03 |

OTHER PUBLICATIONS

Burton et al.: Development of a sensor for non-invasive intracranial pressure measurement in the newborn; J. Biomed. Eng. 1988, vol. 10.
Product Description: Multigon Industries, Inc. 500V Transcranial Doppler.
Product Description: EME TC-TRAK: The First TCD Monitoring Program.
Product Description/Instructions: Medasonics Cerebrovascular Diagnostic System.

Primary Examiner—Francis Jaworski
Attorney, Agent, or Firm—Fliesler, Dubb, Meyer & Lovejoy

[57] ABSTRACT

A transcranial Doppler (TCD) probe fixation assembly is provided comprising an assembly for holding a TCD probe. The probe holding assembly comprises in one embodiment a track assembly and in another embodiment a single bar assembly. The ends of both the track assembly and bar assembly are connected to an annular member. Strap retaining members are provided on the exterior of the annular member for strapping the TCD probe to a patient's head. In use, the position of the probe is selected by moving the probe linearly along the track and bar assemblies and by rotating the track and bar assemblies relative to the annular member. Thereafter, the probe is angulated until a desired signal is obtained, at which point it is locked in place.

20 Claims, 7 Drawing Sheets

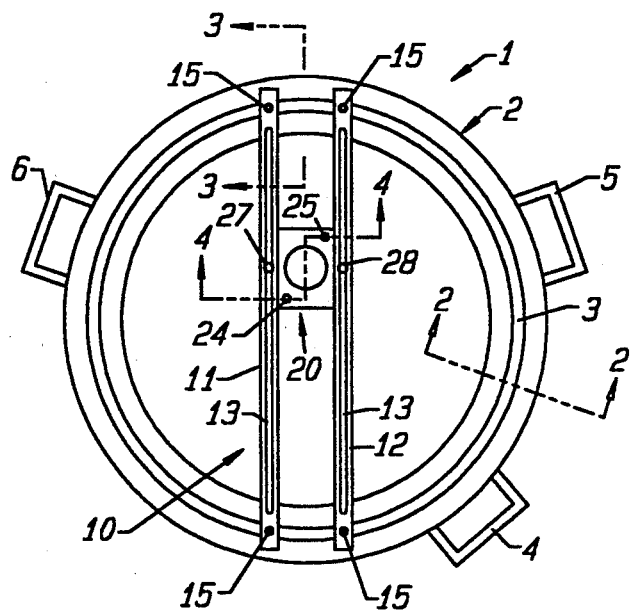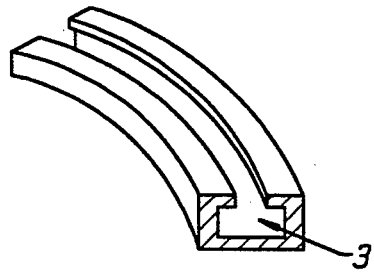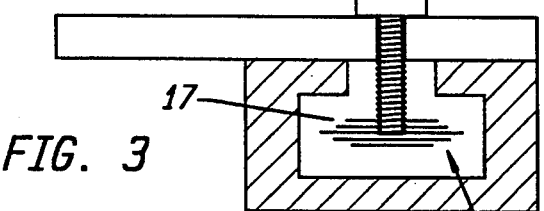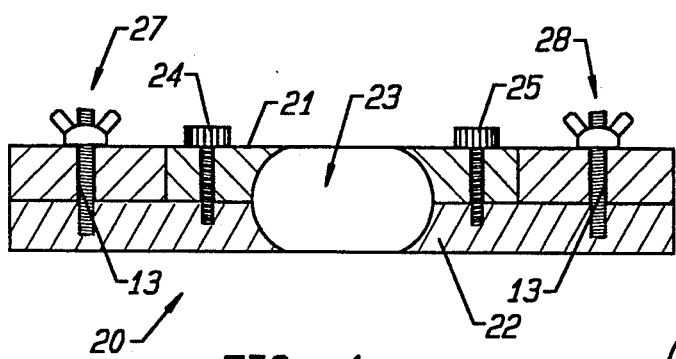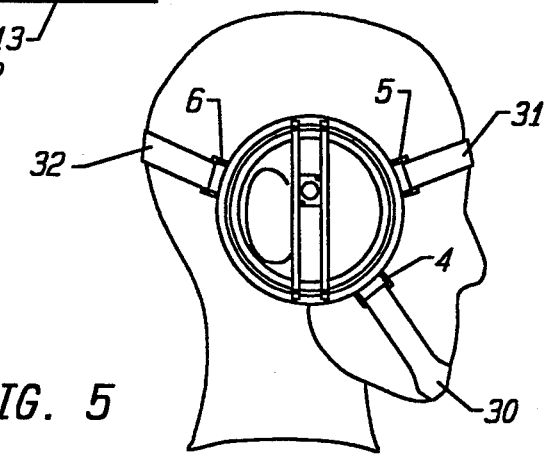

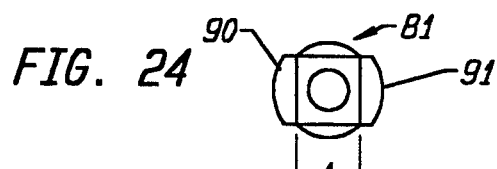
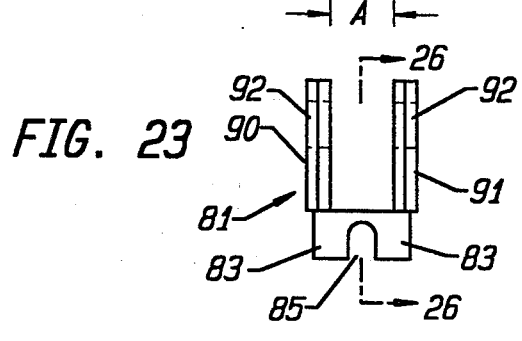
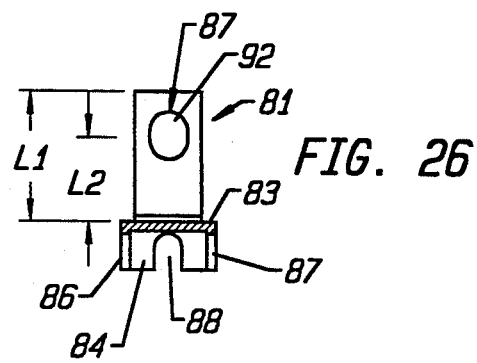
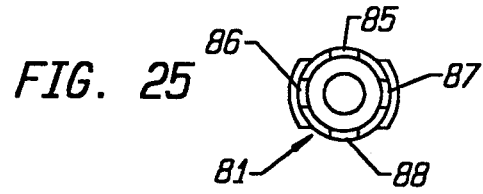
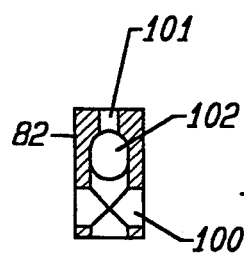
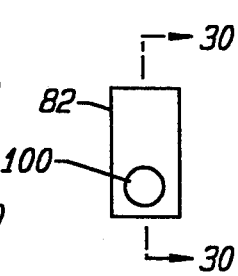
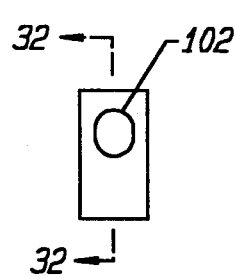
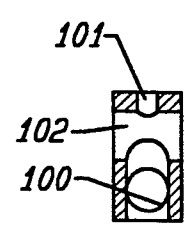
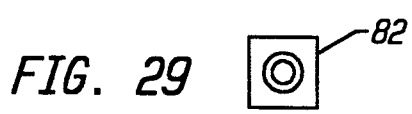
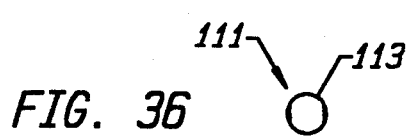
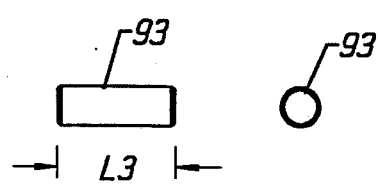
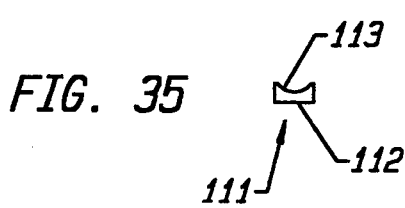
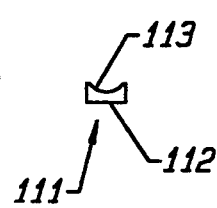

TRANSCRANIAL DOPPLER PROBE WHEEL AND TRACK/BAR FIXATION ASSEMBLY

BACKGROUND OF THE INVENTION

1. Field of the Invention

The present invention relates to transcranial Doppler probe apparatus in general and in particular to an apparatus for selectively placing and fixing a transcranial Doppler probe on a patient's head.

2. Description of the Related Art

Since its introduction in 1982 by Aaslid et al., Noninvasive transcranial doppler ultrasound recording of flow velocity in basal cerebral arteries, *J Neurosurgery* 1982;57:769-74, the transcranial Doppler (TCD), an ultrasonic device for noninvasively and continuously measuring cerebral blood flow velocity, has been an invaluable research tool for investigators of neurophysiology. While great strides have been made using this technology for both research and clinical monitoring applications, one annoying, if seemingly trivial, mechanical problem has continued to plague users of this device. Vast improvements have been made in transcranial Doppler technology in recent years however there is at present no commercially available method of securing the Doppler probe to the head of the subject which has been consistently satisfactory and reliable.

Presently available methods use the following sequence. First, the investigator locates the Doppler signal by manipulating the probe over the appropriate cranial location. Once having found the signal the investigator attempts to secure the position of the probe using any of a variety of crude fixation methods. For example, tape, Velcro TM straps, surgical glue and other items have all been used with varying results. Even experienced users of TCD ultrasonography can at times have difficulty locating the Doppler signal. Once located, translocation or angulation of the probe a fraction of a millimeter in any direction can result in loss or diminution of the signal. Invariably, this is what occurs during the process of securing the probe after location of the signal.

SUMMARY OF THE INVENTION

In view of the foregoing, principal objects of the present invention are a method and apparatus in which the prior known sequence for affixing a TCD probe to a patient's head is reversed.

In accordance with the above objects, a circular device which acts as a frame of reference for a Doppler probe is provided with means for securing the device to a patient's head.

In one embodiment of the present invention, the device comprises a ring-shaped member, a TCD probe holder track assembly and a TCD probe holder assembly.

The ring-shaped member comprises a plurality of loop members which are located about the periphery of the ring-shaped member and a centrally located inverted T-shaped slot. The loop members are provided for strapping the ring-shaped member to a patient's head. The inverted T-shaped slot is provided for slidably attaching the track assembly to the ring-shaped member.

The TCD probe holder track assembly is provided to extend across the diameter of the ring-shaped member and is provided with a pair of track members having a centrally located slot and adjustable track fittings at the ends thereof for engaging interior walls of the inverted T-shaped slot in the ring-shaped member. The track fittings permit the probe holder track assembly to be rotated in a sliding fashion to a selected position relative to the ring-shaped member and then be fixed in the selected position.

The TCD probe holder assembly is provided with a spherical or doughnut-shaped socket formed by a lower locking plate and an upper locking plate and a plurality of adjustable fittings. The locking plates allow for selective angulation of the TCD probe while the fittings are provided for engaging the slot in the tracks of the probe holder track assembly. The TCD probe holder assembly fittings permit the TCD probe holder assembly to be slid in a linear fashion to a selected position on the tracks and then fixed in that position.

Once the ring-shaped member is secured to a patient's head at a selected location, the position of the probe and its angulation with respect to the head can be adjusted and fixed by rotating the probe holder track assembly to a selected position within the ring-shaped member, sliding the probe holder assembly along the tracks of the probe holder track assembly to a selected position and thereafter angulating the probe until a desired signal is obtained. After the desired signal is located from the anterior cerebral artery (ACA), the middle cerebral artery (MCA) or the posterior cerebral artery (PCA), the probe can be locked in position by simply tightening a pair of manually adjustable screws.

In another embodiment of the present invention the ring-shaped member comprises a plurality of loop members which are located about the periphery of the ring-shaped member and a centrally located inverted T-shaped slot. The loop members are provided for strapping the ring-shaped member to a patient's head. The inverted T-shaped slot is provided for slidably attaching a bar assembly to the ring-shaped member.

The TCD probe holder bar assembly is provided to extend across the diameter of the ring-shaped member and is provided with a single bar member having adjustable track fittings at the ends thereof for engaging interior walls of the inverted T-shaped slot in the ring-shaped member. The single bar permits the probe holder assembly to be rotated in a sliding fashion to a selected position relative to the ring-shaped member and then be fixed in the selected position.

The TCD probe holder assembly comprises a probe receiving socket which is mounted on the bar for sliding movement parallel to the axis of the bar and for rotation about an axis of the bar in a plane perpendicular thereto.

In still another embodiment of the present invention the above-described TCD probe holder assembly which is mounted to the bar assembly comprises a U-joint assembly in which the probe holder is allowed to be rotated about a pair of orthogonal axes which lie in planes parallel and perpendicular to the axis of the bar.

With respect to all of the above-described embodiments, once the ring-shaped member is secured to a patient's head at a selected location, the position of the probe and its angulation with respect to the head can be adjusted and fixed by rotating the probe holder or bar assembly to a selected position within the ring-shaped member, sliding the probe holder assembly along the probe holder track or bar assembly to a selected position and thereafter angulating the probe until a desired signal is obtained. After-.the desired signal is located from the anterior cerebral artery (ACA), the middle cerebral artery (MCA) or the posterior cerebral artery (PCA), the probe can be locked in position by simply tightening manually adjustable screws provided therefor.

BRIEF DESCRIPTION OF THE DRAWINGS

The above and other objects, features and advantages of the present invention will become apparent from the following detailed description of the accompanying drawings, in which:

FIG. 1 is a plan view of a transcranial Doppler (TCD) probe wheel and track mounting assembly according to an embodiment of the present invention;

FIG. 2 is a perspective cross-sectional view of a portion of the ring member according to the present invention taken in the direction of lines 2—2 in FIG. 1;

FIG. 3 is a partial cross-sectional view taken in the direction of lines 3—3 of FIG. 1;

FIG. 4 is a cross-sectional view of a probe holder assembly according to the present invention taken in the direction of lines 4—4 of FIG. 1; and FIG. 5 is a side elevation view of the transcranial Doppler (TCD) probe fixation assembly of FIG. 1 strapped to a patient's head according to the present invention.

FIG. 23 is a side elevation view of one of the components of the apparatus of FIG. 19 according to the present invention;

FIG. 24 is a top plan view of FIG. 23;

FIG. 25 is a bottom plan view of FIG. 23;

FIG. 26 is a cross-sectional view taken in the direction of lines 26—26 of FIG. 23;

FIG. 27 is a side elevation view of another component of the apparatus of FIG. 19 according to the present invention;

FIG. 28 is a top plan view of FIG. 27;

FIG. 29 is a bottom plan view of FIG. 27;

FIG. 30 is a cross-sectional view taken in the direction of lines 30—30 of FIG. 27;

FIG. 31 is a side elevation view of FIG. 27;

FIG. 32 is a cross-sectional view taken in the direction of lines 32—32 of FIG. 31;

FIG. 33 is an elevation view of a dowel used for interconnecting the apparatus of FIGS. 23-32 according to the present invention;

FIG. 34 is an end view of FIG. 33;

FIG. 35 is a side elevation view of one of two block members used for coupling the dowel of FIG. 33 to the bar of FIGS. 10-12 in the embodiment of FIG. 19 according to the present invention; and FIG. 36 is a top plan view of the block member of FIG. 35.

DESCRIPTION OF THE PREFERRED EMBODIMENTS

Figure 6:
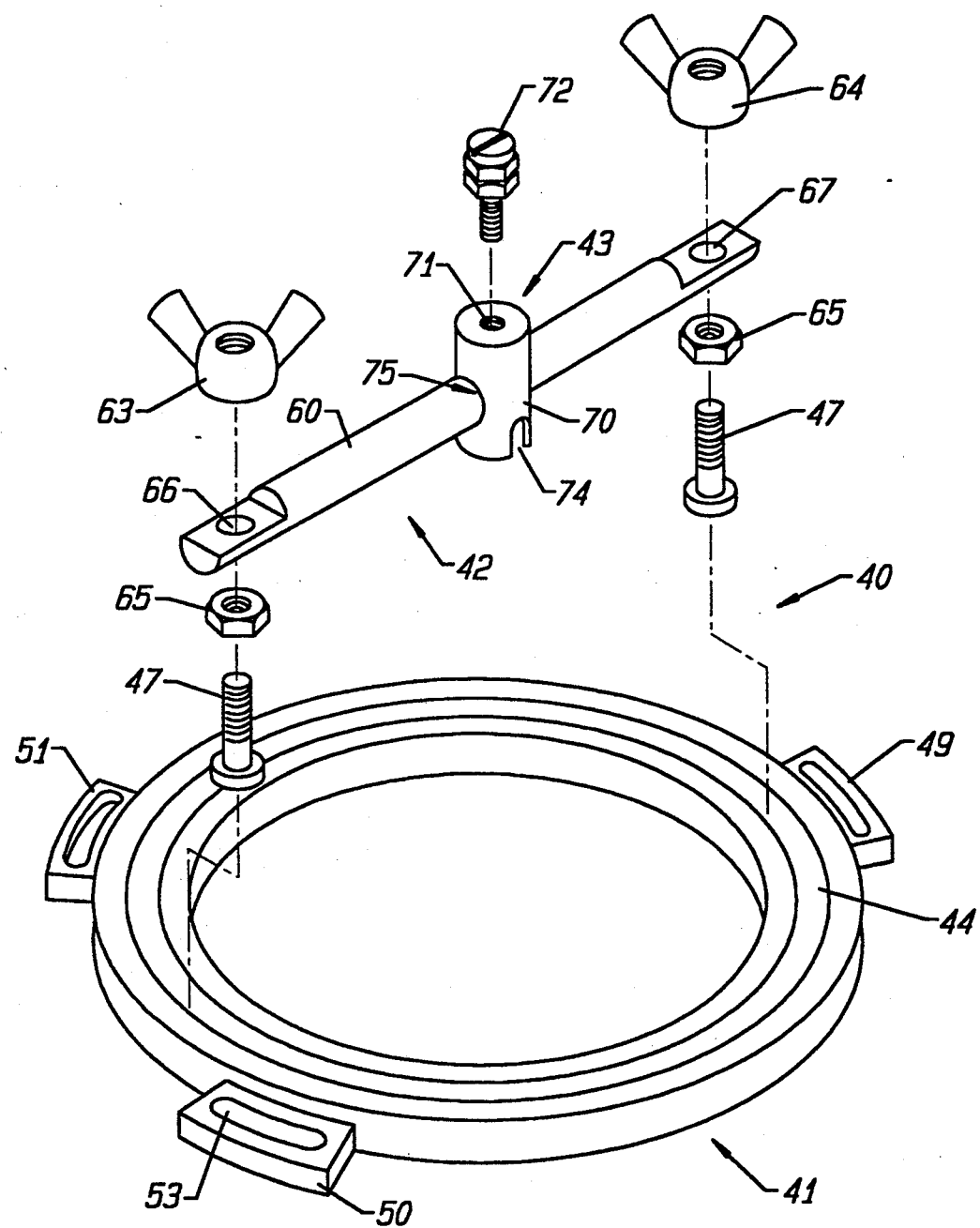
FIG. 6 is a perspective view of a transcranial Doppler (TCD) probe wheel and bar mounting assembly according to another embodiment of the present invention.
Figure 7:
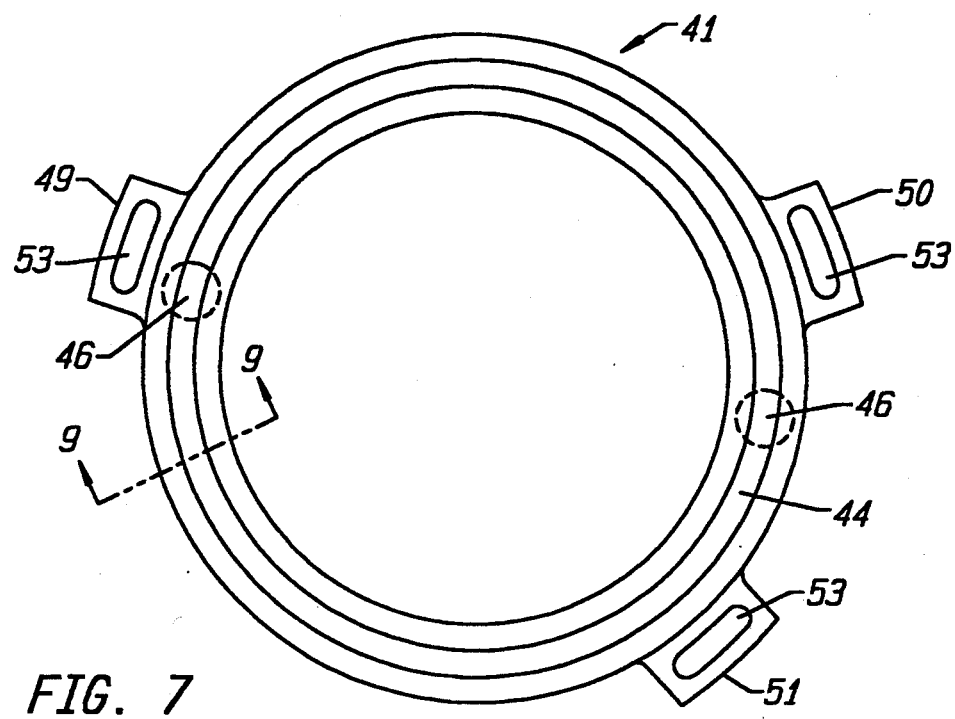
FIG. 7 is a top plan view of the wheel/ring member of FIG. 6.
Figure 8:
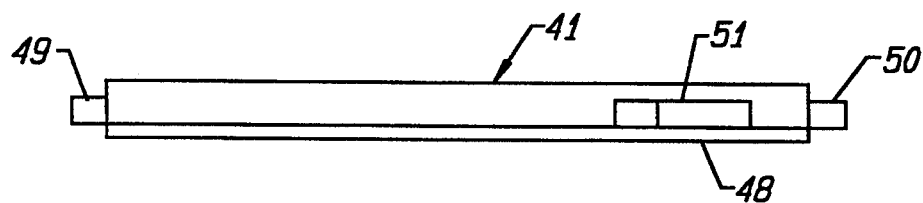
FIG. 8 is a side elevation view of FIG. 7.

Referring to FIG. 1, there is provided in accordance with the present invention a transcranial Doppler (TCD) probe fixation assembly designated generally as 1. In the assembly 1 there is provided a ring-shaped member 2. Centrally located in the member 2, as shown most clearly in FIGS. 2 and 3, there is provided an inverted T-shaped slot 3. At selected positions about and extending outwardly from the periphery of the member 2 there is provided a plurality of strap engaging members 4, 5 and 6.

In the interior of the member 2 there is provided a track assembly designated generally as 10. The track assembly 10 comprises a pair of track members 11 and 12. Each of the track members 11 and 12 is provided with a centrally located slot 13. The slot 13 is provided by cutting through the center of the track members along substantially most, but not all, of their lengths so as to effectively cut each of the track members in half except for short end portions thereof. At each end of the track members 11 and 12 there is provided an adjustable fitting designated generally as 15. As shown in FIG. 3, the fitting 15 comprises a central threaded member 16. At the lower end of the member 16 there is provided a washer-like member 17. At the upper end of the member 16 there is provided a thumb-actuated member 18. As will be further described below, when the thumb-actuated member 18 is rotated so as to draw the washer-like member 17 against the interior surface of the inverted slot 3, the track members 11 and 12 are fixed in position relative to the ring-shaped member 2.

Centrally located between the track members 11 and 12 there is provided a transcranial Doppler (TCD) probe holding assembly designated generally as 20. As shown in FIG. 4, assembly 20 comprises an upper TCD probe locking plate 21 and a lower TCD probe locking plate 22 having a generally planar base surface. The locking plates 21 and 22 include a spherical or doughnut-shaped socket 23 for receiving and holding a TCD probe (not shown). On opposite sides of the socket 23 there is provided a pair of screw members 24 and 25. The screw members 24 and 25 are provided for tightening or threadably attaching the upper locking plate 21 to the lower locking plate 22. Outside the upper plate 21 there is provided a pair of thumb screws 27 and 28. Screws 27 and 28 project through the slots 13 in the track members 11 and 12 and threadably engage the lower plate 22 for locking the assembly 20 in a selected position on the track members 11 and 12.

Referring to FIG. 5, in use the ring-shaped member 2 is secured to a patient's head at a selected location by means of a chin strap 30, a brow strap 31 and a rear head strap 32 which are caused to be looped through or otherwise engage the members 4, 5 and 6, respectively. Once the ring-shaped member is secured to a patient's head as shown in FIG. 5, the position of the probe (not shown) and its angulation with respect to the head can be adjusted and fixed by rotating the track assembly 10 within the ring-shaped member 2. This is done by loosening the thumb-screw fittings 15 at each end of the track members 11 and 12 rotating the track members 11 and 12 about an axis perpendicular to the plane of the ring-shaped member 2 and then tightening the fitting 15 when the track members 11 and 12 are in their desired position. After the track members 11 and 12 are in their desired position, the probe holding assembly 20 can be slid in a linear fashion along the track members 11 and 12 to a selected position by loosening the screw members 27 and 28, sliding the probe assembly 20 to the selected position and again tightening the screw members 27 and 28. When the screw members 27 and 28 are tightened they clamp the lower probe locking plate 22 to the track members 11 and 12, respectively. Once the probe holding assembly 20 is in the selected position, the TCD probe located in the socket 23 can be angulated relative to the planar base thereof by loosening the screws 24 and 25 and thereafter angulating the probe until the desired signal is obtained. After the desired signal is located from the anterior cerebral artery (ACA), the middle cerebral artery (MCA) or the posterior cerebral artery (PCA), the probe can be locked in position by simply tightening the manually adjustable screws 24 and 25.

Because the circular member 2 which is designed to fit around the ear of the patient can be moved in any direction with respect to the ear prior to fixation, a single size is adequate for patients over a large age range, although it is likely that for very small patients or very large patients, smaller and larger models may be desirable. An additional advantage of the fixation assembly according to the present invention is that since the assembly is symmetrical with respect to its strap supports, a single device can be used for both the left and right sides.

The contour of the head on which the circular member rests can be described by three planar areas of different elevation. These areas are the ramus of the mandible, the zygomatic arch, and the surface of the cranium superior and posterior to the pinna. Since any circle resting on a tripodial support must, by simple physical principles, be stable, the TCD probe fixation assembly according to the present invention rests securely on the head of a patient.

Referring to FIGS. 6–15, there is provided in accordance with another embodiment of the present invention a transcranial Doppler (TCD) probe wheel and bar mounting assembly designated generally as 40 comprising a wheel/ring assembly 41, a single bar assembly 42 and a TCD probe holder assembly 43. Centrally located in the member 41 there is provided an inverted T-shaped slot 44. At diametrically opposed positions in the bottom wall of the slot 44 there is provided a pair of enlarged bolt head receiving holes 46 for receiving the head of a bolt 47, as will be further described below.

Figure 9:
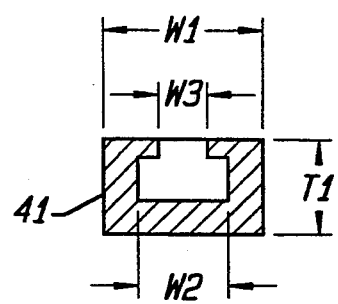
FIG. 9 is a cross-sectional view taken in the direction of lines 9—9 in FIG. 7.

As seen in FIG. 9, ring member 41 has a width W1 of approximately 0.45 inch and a thickness T1 of approximately 0.275 inch. The major width W2 of the slot 44 as shown in FIG. 9 is approximately 0.25 inch. The minor width W3 of the slot 44 is approximately 0.135 inch. The diameter D1 of each of the holes 46 is approximately 0.25 inch.

Mounted to the bottom of the ring member 41 there is provided a layer of foam 48 approximately 0.25 inch thick. Selectively spaced about the periphery of the ring member 41 there is provided a plurality of strap retaining loop members 49, 50 and 51 which extend outwardly from the outer wall of the ring member 41 a distance of approximately 0.331 inch. Each of the loop members 49–51 have a generally rectangular strap receiving hole 53 which is approximately 0.15 inch wide and 0.5 inch long. The members 50 and 51 are approximately 1.91 inches apart and the member 52 is on the opposite side of the ring member 41 approximately diametrically opposed from a point midway between the members 50 and 51.

Figure 11:
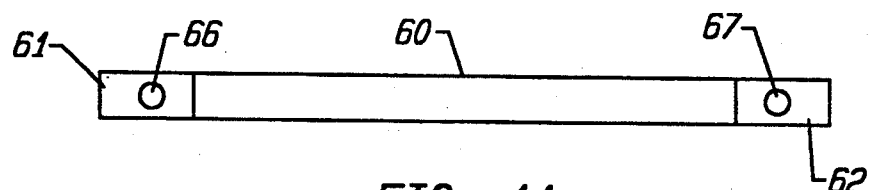
FIG. 11 is a top plan view of FIG. 10.
Figures 10, 12:
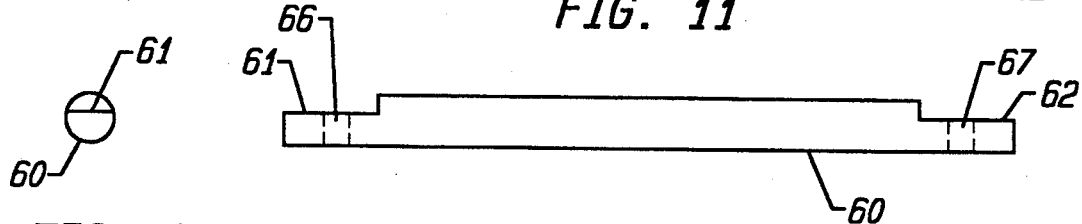
FIG. 10 is a side elevation view of the bar in the bar assembly of FIG. 6 according to the present invention.
FIG. 12 is an end view of FIG. 11.
Figure 14:
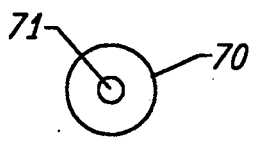
FIG. 14 is a top plan view of FIG. 13.
Figure 13:
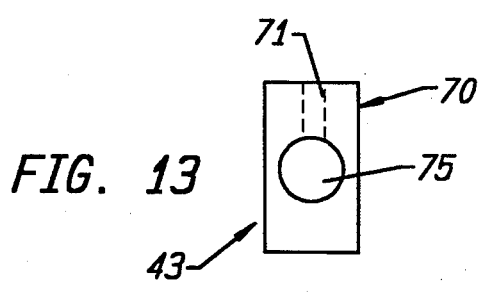
FIG. 13 is an elevation view of the TCD probe holder of FIG. 6.
Figure 16:
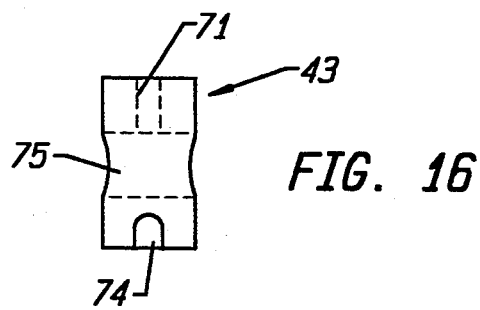
FIG. 16 is a side elevation view of FIG. 13.
Figure 15:
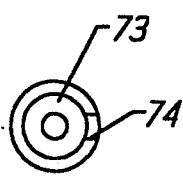
FIG. 15 is a bottom view of FIG. 13.

Referring to FIGS. 10–12, the bar assembly 42 comprises a bar member 60 which is approximately 0.25 inch in diameter. At each end thereof the bar member 60 is provided with a flat surface 61 and 62, respectively, against which a thumbscrew 63 and 64, respectively, is allowed to bear when the thumbscrew is threaded on the bolt 47 for tightening the bar assembly 42 against the ring member 41. A nut 65 is also provided on each of the bolts 47 beneath the bar 60 to serve as a tightening member. The bolts 47 pass through holes 66 and 67 provided therefor in the flattened ends of the bar 60.

Referring to FIGS. 13–16, there is provided in the TCD probe holder assembly 43 a probe holder 70 having in its upper end a threaded hole 71 for receiving a set screw 72 as seen in FIG. 6, and in its lower end a cylindrical socket 73. In a wall of the socket 73 there is provided a hole 74 for a TCD probe lead. In the center of the probe 70 there is provided a hole 75 having a diameter of approximately 0.254 inch for receiving the bar 60 of the assembly 42.

Referring to FIGS. 17–35, there is provided in another embodiment of the present invention a TCD probe mounting assembly designated generally as 77 comprising a TCD probe holder designated generally as 80 which is mounted on the bar 60 of the assembly 42 and may be used in place of the TCD probe holder assembly 43 of FIG. 6 to provide in addition to the degrees of freedom of the TCD probe holder 70 of FIG. 6, angulation of the TCD probe in a plane parallel to the axis of the bar 60. For convenience the probe holder 80 is sometimes descriptively referred to as a U-joint probe holder.

Figure 20:
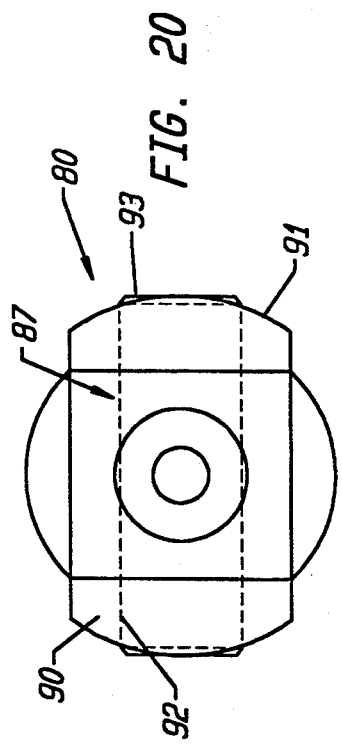
FIG. 20 is a top plan view of FIG. 19.

Referring to FIGS. 23–35, the U-joint probe holder 80 comprises a generally U-shaped outer member 81, and an elongated interior box-shaped member 82. At its lower end the member 81 is provided with a TCD probe receiving section 83 having a socket 84 and a plurality of holes 85, 86, 87 and 88 for allowing a lead of a TCD probe to pass therethrough. Extending upwardly from the probe receiving socket 83 there is provided a pair of spaced leg members 90 and 91. Near the top end of each of the members 90, 91 there is provided a hole 92 for receiving a dowel 93 as shown in FIG. 20 and FIGS. 33 and 34. As seen in FIG. 24, the distance A between the legs 90, 91 is approximately 0.441 inch. As seen in FIG. 26, the length L1 of the legs 90, 91 is approximately 0.85 inch and the length L2 of the legs to the center of the hole 92 is approximately 0.60 inch. As more clearly shown in FIGS. 19–21, during assembly the dowel 93, which has a diameter of approximately 0.25 inch and a length of approximately 0.75 inch, is press-fit in the holes 92.

Figure 17:
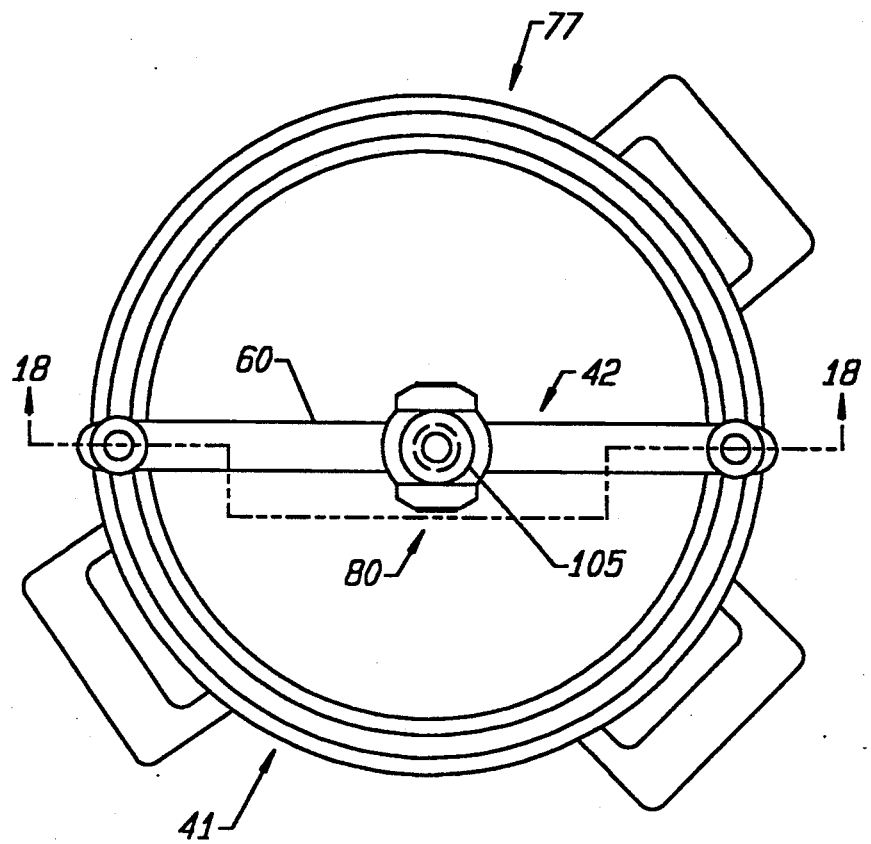
FIG. 17 is a top plan view of a TCD probe wheel and bar assembly comprising a U-joint probe holder assembly according to another embodiment of the present invention.
Figure 18:
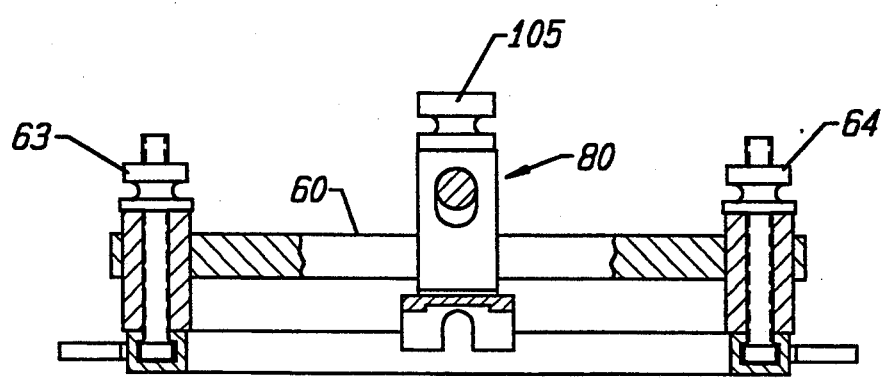
FIG. 18 is a cross-sectional view taken in the direction of lines 18—18 in FIG. 17.
Figure 22:
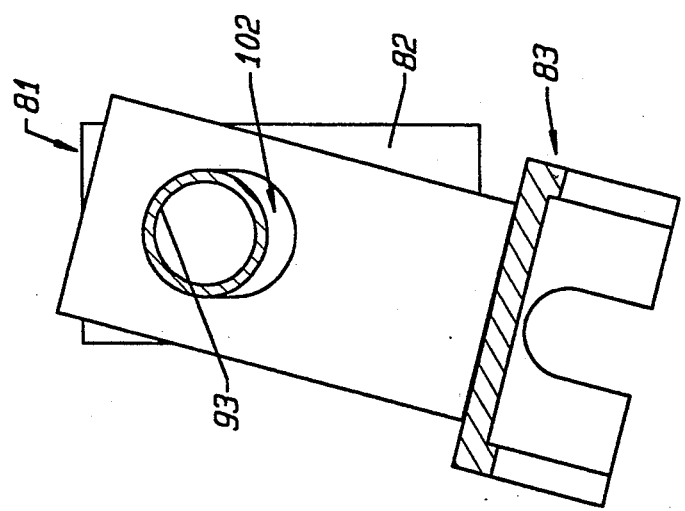
FIG. 22 is a side elevation view taken in the direction of lines 21—21 of FIG. 19 with one of the parts of the apparatus of FIG. 19 being rotated relative to another of the parts of the apparatus of FIG. 19.
Figure 21:
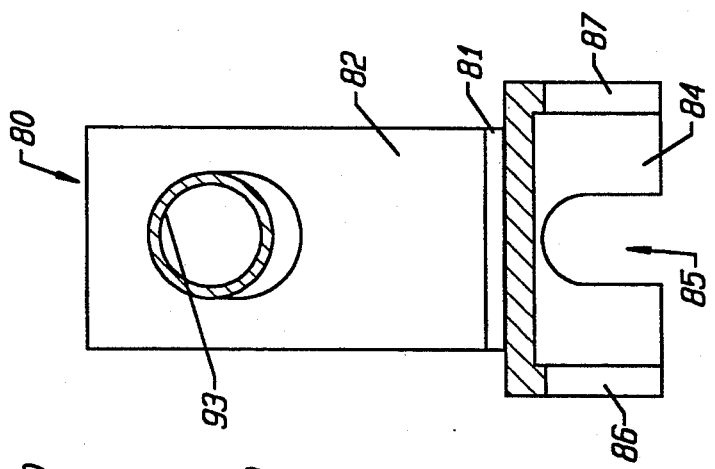
FIG. 21 is a side elevation cross-sectional view taken in the direction of lines 21—21 in FIG. 19.

Referring to FIGS. 27-32, there is provided in the interior member 82 a hole 100 having a diameter of approximately 0.257 inch for receiving the bar 60 having a diameter of approximately 0.250 inch. In the top of the member 82 there is provided a threaded hole 101 for receiving a set screw 105 as shown in FIGS. 17 and 18 which corresponds to set screw 72 of FIG. 6. Orthogonal to the hole 100 and near the top of the member 82 there is provided an elongated hole 102 which is provided for receiving the dowel 93 in a slip-fit manner. The hole 102 is elongated in order to allow relative movement between the interior member 82 and dowel 93 as will be described below.

Figure 19:
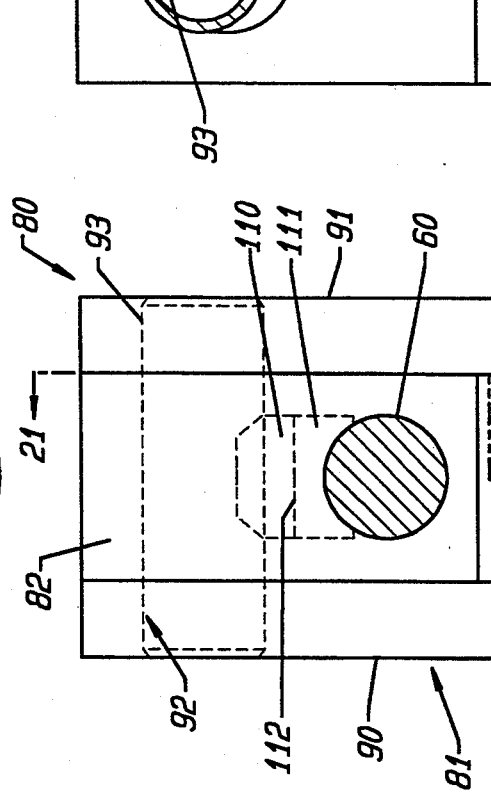
FIG. 19 is a side elevation view of the TCD probe holder assembly of FIGS. 17 and 18.

Referring to FIGS. 33 and 34 and FIG. 19, there is provided between the dowel 93 and the bar 60 a pair of circular mounting members 110 and 111, only one of which (member 111) is shown in FIGS. 35 and 36. Each of the members 110 and 111 have a flat surface 112 and a concave surface 113 for receiving, respectively, dowel 93 and bar 60.

After the members 110 and 111 are placed between the dowel 93 and the bar 60 as shown in FIG. 19, the set screw 105 corresponding to set screw 72 is threaded in the hole 101 and screwed down against the dowel 93 which causes the dowel 93 and exterior member 81 to be clamped to the bar 60 with the blocks 110 and 111 clamped therebetween. In this fashion the TCD probe holder assembly 80 is clamped to the bar 60 while at the same time the assembly 80 is allowed to be rotated, i.e. angulated, in a plane perpendicular to and parallel with the axis of the bar 60 while friction holds it in the position to which it is moved.

While preferred embodiments of the present invention are described above, it is contemplated that numerous modifications may be made thereto for particular applications without departing from the spirit and scope of the present invention. Accordingly, it is intended that the embodiments described be considered only as illustrative of the present invention and that the scope thereof should not be limited thereto but be determined by reference to the claims hereinafter provided.

What is claimed is:

1. A transcranial Doppler (TCD) probe fixation assembly comprising:
   a TCD probe carrier;
   elongated track means for supporting said carrier;
   an annular member for supporting the ends of said track means;
   means for permitting said TCD probe carrier to be moved linearly from a first position to a second position along said track means;
   means for permitting the track means to be rotated from a first position to a second position about an axis perpendicular to the plane of said annular member; and
   means for permitting a change in the angle of the axis of the TCD probe relative to a line perpendicular to said plane.

2. A TCD probe fixation assembly according to claim 1 wherein said means for holding a TCD probe in a predetermined plane on the head of a patient comprises:
   means on said annular member for retaining a plurality of strap members.

3. A TCD probe fixation assembly according to claim 2 wherein said strap member retaining means comprises a first, a second and a third strap retaining means located at selected locations on the periphery of said annular member.

4. A TCD probe fixation assembly according to claim 3 wherein said first, said second and said third strap retaining means comprises means for retaining a chin strap, a brow strap and a rear head strap, respectively.

5. A TCD probe fixation assembly according to claim 2 wherein said means for holding a TCD probe in a predetermined plane on the head of a patient comprises surgical tape or the like.

6. A TCD probe fixation assembly according to claim 1 wherein said track means and said annular member each comprises an elongated slot and wherein said means for permitting said TCD probe carrier to be moved linearly from a first position to a second position along said track means comprises first adjustable locking means for locking said TCD probe carrier to said elongated slot in said track means and said means for permitting the track means to be rotated from a first position to a second position about an axis perpendicular to the plane of said annular member comprises second adjustable locking means for locking the ends of said track means to said elongated slot in said annular member.

7. A TCD probe fixation assembly according to claim 6 wherein said first and second adjustable locking means comprises a first and second thumb screw means, said slot in said annular member comprises an inverted T-shaped slot, and the second thumb screw means comprises a washer-like member on the interior end of the second thumb screw means for engaging an interior wall of the inverted T-shaped slot when the second thumb screw means is tightened.

8. A TCD probe fixation assembly according to claim 1 wherein
   said means for permitting a change in the angle of the axis of the TCD probe relative to a line perpendicular to said plane comprises:
   means on said TCD probe carrier for selectively permitting angular movement of said axis of said TCD probe.

9. A transcranial Doppler (TCD) probe fixation assembly according to claim 1 wherein said TCD probe carrier comprises an upper probe locking plate and a lower probe locking plate with a cavity for receiving and holding a TCD probe therein and said means on said TCD probe carrier for permitting a change in the angle of said axis of said TCD probe comprises means for selectively tightening said upper and lower probe locking plates together after said TCD probe has been move to a selected angle for holding said TCD probe at said selected angle.

10. A TCD probe fixation assembly according to claim 9 wherein said means for selectively tightening said upper and lower probe locking plates together comprises screw means.

11. A transcranial Doppler (TCD) probe fixation assembly comprising:
   a TCD probe carrier;
   an elongated bar-shaped member for supporting said carrier;
   an annular member for supporting the ends of said bar-shaped member;
   means for permitting said TCD probe carrier to be moved linearly from a first position to a second position along said bar-shaped member;

means for permitting the bar-shaped member to be rotated from a first position to a second position about an axis perpendicular to the plane of said annular member; and means for permitting a change in the angle of the axis of the TCD probe relative to a line perpendicular to said plane.

12. A TCD probe fixation assembly according to claim 11 wherein said means for holding a TCD probe in a predetermined plane on the head of a patient comprises:

means on said annular member for retaining a plurality of strap members.

13. A TCD probe fixation assembly according to claim 12 wherein said strap member retaining means comprises a first, a second and a third strap retaining means located at selected locations on the periphery of said annular member.

14. A TCD probe fixation assembly according to claim 13 wherein said first, said second and said third strap retaining means comprises means for retaining a chin strap, a brow strap and a rear head strap, respectively.

15. A TCD probe fixation assembly according to claim 1 wherein said means for holding a TCD probe in a predetermined plane on the head of a patient comprises surgical tape or the like.

16. A TCD probe fixation assembly according to claim 11 wherein said TCD probe carrier comprises a hole for mounting said TCD carrier to said bar-shaped member and said annular member comprises an elongated slot and wherein said means for permitting said TCD probe carrier to be moved linearly from a first position to a second position along said bar-shaped member comprises first adjustable locking means for selectively locking said TCD probe carrier to said bar-shaped member after said TCD probe is moved in a sliding manner on said bar-shaped member to a selected position and said means for permitting the bar-shaped member to be rotated from a first position to a second position about an axis perpendicular to the plane of said annular member comprises second adjustable locking means for locking the ends of said bar-shaped member to said elongated slot in said annular member.

17. A TCD probe fixation assembly according to claim 16 wherein said first adjustable locking means comprises a setscrew and said second adjustable locking means comprises a thumb screw means, said slot in said annular member comprises an inverted T-shaped slot, and the thumb screw means comprises a washer-like member on the interior end of the thumb screw means for engaging an interior wall of the inverted T-shaped slot when the thumb screw means is tightened.

18. A transcranial Doppler (TCD) probe fixation assembly comprising:

a TCD probe carrier;

an elongated bar-shaped member for supporting said carrier; and an annular member for supporting the ends of said bar-shaped member, said TCD probe carrier including a first member mounted on said bar-shaped member for sliding movement in a direction parallel and for rotation in a plane perpendicular to the axis of said bar-shaped member, a second member coupled to said first member for rotation about an axis perpendicular to the axis of said bar-shaped member, said second member having a cavity in the lower end thereof for receiving and holding a TCD probe therein, and means for selectively locking said TCD probe carrier to said bar-shaped member after said TCD probe has been moved to a selected angle for holding said TCD probe at said selected angle.

19. A TCD probe fixation assembly according to claim 18 wherein said means for selectively locking said TCD probe carrier to said bar-shaped member comprises means for selectively locking said means for coupling said first member to said second member to said bar-shaped member in a friction tight manner.

20. A TCD probe fixation assembly according to claim 19 wherein said means for selectively locking said means for coupling said first member to said second member to said bar-shaped member in a friction tight manner comprises a set screw.

* * * * *

UNITED STATES PATENT AND TRADEMARK OFFICE
CERTIFICATE OF CORRECTION

PATENT NO. : 5,409,005
DATED : April 25, 1995
INVENTOR(S) : Bruno Bissonnette et al.

It is certified that error appears in the above-indentified patent and that said Letters Patent is hereby corrected as shown below:

Column 2, line 67, "After-.the" should be --After the--;

Column 8, line 9, "2" should be --1--;

Column 9, line 25, "claim 1" should be --claim 11--.

Signed and Sealed this

Fourteenth Day of May, 1996

Attest:

BRUCE LEHMAN

Attesting Officer    Commissioner of Patents and Trademarks